(12) United States Patent
Feldmann et al.

(10) Patent No.: US 10,114,293 B2
(45) Date of Patent: Oct. 30, 2018

(54) ILLUMINATION SYSTEM AND PROJECTION OBJECTIVE OF A MASK INSPECTION APPARATUS

(75) Inventors: Heiko Feldmann, Aalen (DE); Erik Matthias Sohmen, Aalen (DE); Joachim Stuehler, Aalen (DE); Oswald Gromer, Heidenheim (DE); Ulrich Mueller, Aalen (DE); Michael Layh, Alttusried (DE); Markus Schwab, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 1553 days.

(21) Appl. No.: 13/587,077

(22) Filed: Aug. 16, 2012

(65) Prior Publication Data

US 2013/0038850 A1    Feb. 14, 2013

Related U.S. Application Data

(63) Continuation of application No. PCT/EP2011/052184, filed on Feb. 15, 2011.
(Continued)

(30) Foreign Application Priority Data

Feb. 22, 2010   (DE) .................. 10 2010 009 022

(51) Int. Cl.
*G03F 7/20*  (2006.01)
*G01N 21/956*  (2006.01)
*G03F 1/84*  (2012.01)

(52) U.S. Cl.
CPC ....... *G03F 7/70091* (2013.01); *G01N 21/956* (2013.01); *G03F 1/84* (2013.01); *G01N 2021/95676* (2013.01)

(58) Field of Classification Search
CPC ........ G01N 21/956; G01N 2021/95676; G03F 1/84; G03F 7/70091
See application file for complete search history.

(56) References Cited

U.S. PATENT DOCUMENTS 5,528,360 A * 6/1996 Kohno ............... G01N 21/8901
                                                      356/237.5
5,712,698 A   1/1998 Poschenrieder et al.
(Continued)

FOREIGN PATENT DOCUMENTS

EP   1 300 676 A1   4/2003   ........... G01N 21/956
JP   09-325501     12/1997   ............... G06F 7/20
(Continued)

OTHER PUBLICATIONS

Japanese Office Action for Application No. 2012-554285 dated Sep. 13, 2013 (4 pages).
(Continued)

*Primary Examiner* — Steven H Whitesell Gordon
(74) *Attorney, Agent, or Firm* — Fish & Richardson P.C.

(57) ABSTRACT

An illumination system and a projection objective of a mask inspection apparatus are provided. During operation of the mask inspection apparatus, the illumination system illuminates a mask with an illumination bundle of rays having a centroid ray that has a direction dependent on the location of the incidence of the illumination bundle of rays on the mask.

45 Claims, 9 Drawing Sheets

Related U.S. Application Data

(60) Provisional application No. 61/306,624, filed on Feb. 22, 2010.

(56) References Cited

U.S. PATENT DOCUMENTS

| | | | |
|---|---|---|---|
| 6,268,093 B1 | 7/2001 | Kenan et al. | |
| 7,355,678 B2 | 4/2008 | Hudyma et al. | 355/67 |
| 7,623,620 B2 | 11/2009 | Mann et al. | 378/43 |
| 2001/0046039 A1 | 11/2001 | Kudo | |
| 2005/0083515 A1 | 4/2005 | Naulleau | 356/124 |
| 2005/0088760 A1 | 4/2005 | Mann et al. | 359/730 |
| 2005/0201514 A1* | 9/2005 | Mann | G21K 7/00 378/43 |
| 2007/0132989 A1 | 6/2007 | Kaller et al. | 356/239.1 |

FOREIGN PATENT DOCUMENTS

| | | | |
|---|---|---|---|
| JP | 11-219891 | 8/1999 | H01L 21/027 |
| JP | 11-354404 | 12/1999 | H01L 21/027 |
| JP | 2000-269114 | 9/2000 | H01L 21/027 |
| JP | 2001-235853 | 8/2001 | G03F 1/08 |
| JP | 2009-252818 | 10/2009 | H01L 21/027 |
| WO | WO 03/096356 | 11/2003 | |

OTHER PUBLICATIONS

Feldmann et al., "Actinic Review of EUV Masks," Proc. of SPIE vol. 7636, 76361C, Feb. 24, 2010.
International Search Report and Written Opinion of the International Searching Authority, International Application No. PCT/EP2011/052184, 10 pages, dated May 19, 2011.
Office Action, German Patent Application No. 10 2010 009 022.0, English translation included, 12 pages, dated Oct. 5, 2010.

* cited by examiner

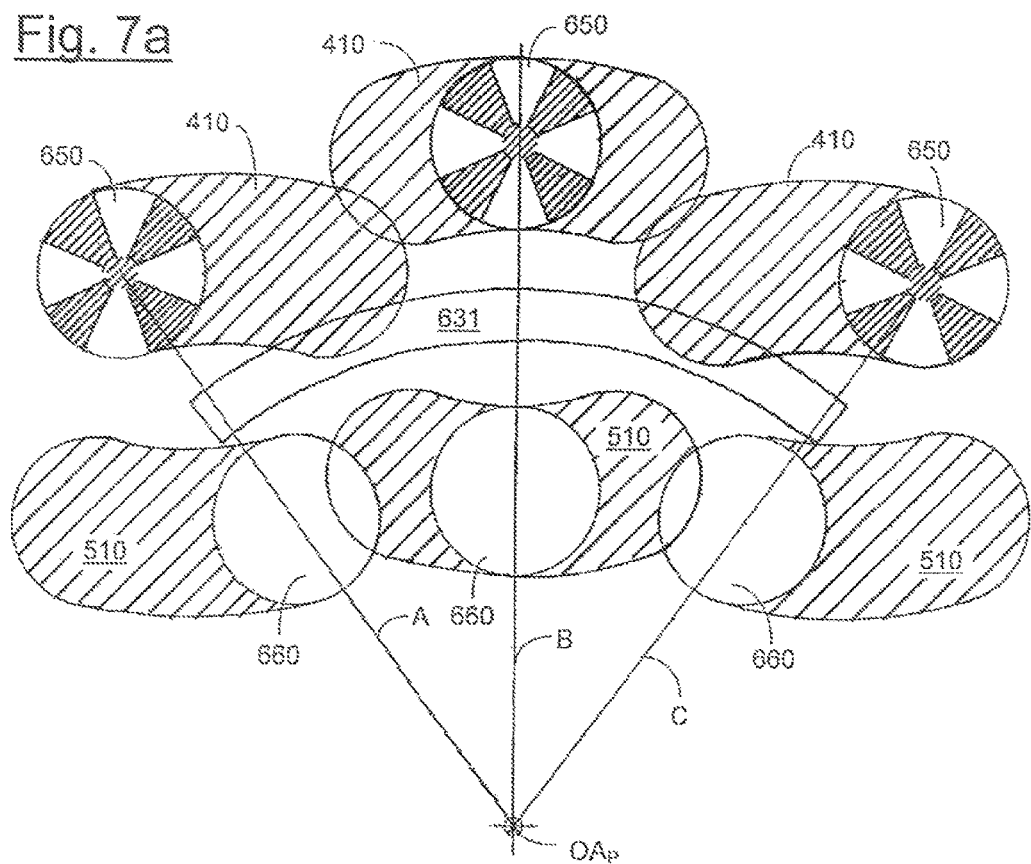
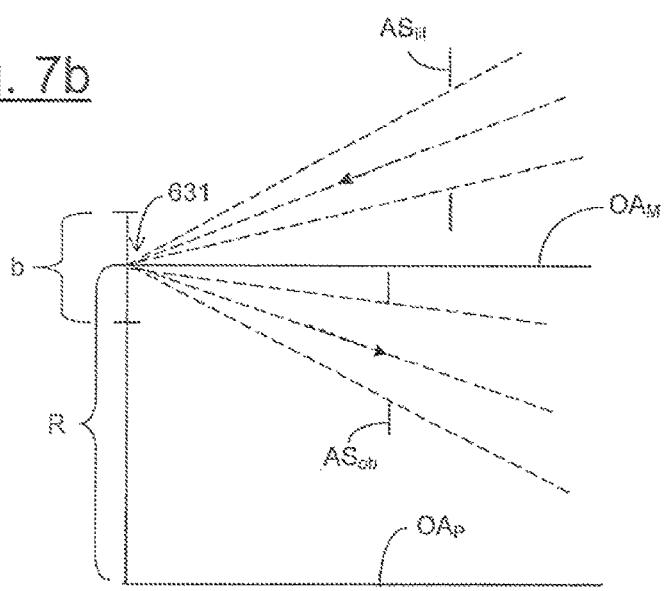

Fig. 8
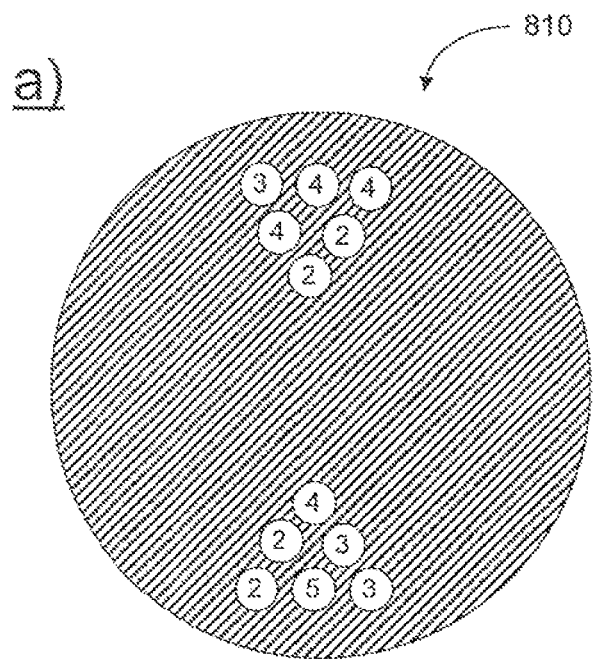
a)
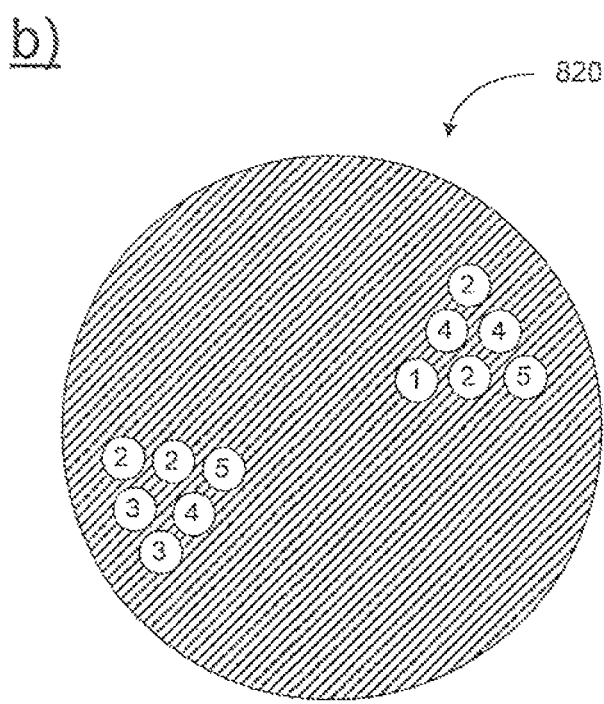
b)

ILLUMINATION SYSTEM AND PROJECTION OBJECTIVE OF A MASK INSPECTION APPARATUS

CROSS REFERENCE TO RELATED APPLICATIONS

This application is a continuation of and claims priority to International patent application PCT/EP2011/052184, filed on Feb. 15, 2011, which claims priority to U.S. provisional patent application 61/306,624, filed on Feb. 22, 2010 and German patent application 10 2010 009 022.0, filed on Feb. 22, 2010. Each of these applications is incorporated by reference in its entirety.

FIELD

The disclosure concerns an illumination system and a projection objective of a mask inspection apparatus.

BACKGROUND

Microlithography is used for the production of microstructured components such as, for example, integrated circuits or liquid crystal displays (LCDs). The microlithography process is carried out in what is referred to as a projection exposure apparatus having an illumination system and a projection objective. In that case the image of a mask (also referred to as a reticle) illuminated by the illumination system is projected by means of the projection objective on to a substrate (for example, a silicon wafer) which is coated with a light-sensitive layer (photoresist) and arranged in the image plane of the projection objective in order to transfer the mask structure on to the light-sensitive coating on the substrate. Mirrors are used as optical components for the imaging process in projection objectives designed for the extreme ultra-violet (EUV) range, that is to say at wavelengths of, for example, about 13 nm or about 7 nm, due to the lack of availability of suitable translucent refractive materials.

In the lithography process unwanted defects on the mask have a particularly detrimental effect as they can be reproduced with each illumination step and there is thus the danger that in the worst-case scenario the entire production of semiconductor components is unusable. It is therefore a matter of great significance for the mask to be checked for adequate imaging capability before use thereof in mass production. In that respect the changeover from vacuum ultra-violet (VUV) systems to EUV systems is linked not only to changes in the materials and process steps used, but in particular also to a higher level of sensitivity (typically by four times) of the reflectively designed EUV mask, in relation to topological defects, in comparison with conventional VUV masks.

In that respect the problem which inter alia arises in practice is that, depending on the respective form of the defects and the position thereof relative to the structure to be imaged, in the mask, deviations which are difficult to predict occur in the imaging process. Therefore direct analysis of the imaging effect of possible defect positions is desirable for minimizing the mask defects and for implementing successful mask repair. There is thus a need for the mask to be quickly and easily tested, more specifically as far as possible under the same conditions as occur really in the projection exposure apparatus. It is to be observed in that respect that different degrees of coherence of the light, different illumination settings and greater and greater numerical apertures involving values of NA=0.35 and above are set in the illumination system of current EUV systems, which in practice represents a demanding challenge in terms of emulation or reproduction of the imaging procedure of the projection exposure apparatus in mask inspection.

SUMMARY

The disclosure provides an illumination system and a projection objective of a mask inspection apparatus, which permit more accurate emulation of the conditions occurring in the projection exposure apparatus.

In an aspect, the disclosure concerns an illumination system of a mask inspection apparatus, wherein the illumination system in operation of the mask inspection apparatus illuminates a mask with an illumination bundle of rays which has a centroid ray, wherein said centroid ray has a direction dependent on the location of the incidence of the illumination bundle of rays on the mask.

In that respect the term "centroid ray" is used in accordance with the usual terminology to denote the energy mean over all subrays of a beam.

The centroid ray of the illumination bundle of rays is of a direction dependent on the location of the incidence of the illumination bundle of rays on the mask. This makes it possible for the pupil illumination of the projection objective to be more exactly emulated. For greater understanding attention is firstly directed to FIGS. 1 through 3 to explain the underlying concept of the present disclosure.

The reference to a variation in the direction of the centroid ray in dependence on the location on the mask is preferably used to denote a variation in respect of which the maximum angle between the centroid rays of two bundle of rays which are incident on different locations on the mask is at least 1°. In some embodiments, the maximum angle between the centroid rays of two bundles of rays incident on different locations on the mask is at least 3°, in particular at least 5°, further particularly at least 10° and further particularly at least 15°.

In another approach the maximum angle between the planes of incidence of two bundles of rays incident on different locations on the mask is at least 3°, in particular at least 5°, further particularly at least 10° and further particularly at least 15°.

In an embodiment a mask which is analyzed in operation of the mask inspection apparatus is designed for use with an illumination region, in the shape of a segment of a ring, in a projection exposure apparatus.

In a lithography process the entire mask is scanned by a scanner slot which in the case of conventional (VUV) systems is typically of a rectangular geometry but which in the case of EUV systems is of a geometry in the shape of a segment of a ring. The background here is that the EUV optical system has a rotationally symmetrical optical design, but in the lithography process only a small portion of that annular field is used, which is comparatively far away from the optical axis. In addition, when using a reflective EUV mask, it is known that to separate the illumination system and the projection objective it is necessary for the illumination bundle of rays to be directed at a finite angle of incidence on to the mask or the reticle, in which case (without the disclosure being restricted thereto) a typical angle in respect of the centroid ray relative to the surface normal on the mask can be 6° in present scanners.

FIGS. 1 through 3 each show an object field 110 in the shape of a segment of a ring, on a mask 101 having a region 102 with structures to be imaged. In FIG. 1 the position which is currently being illuminated is at the center of the object field 110, whereas the position which is currently being illuminated in FIG. 2 is in the region of the left-hand edge of the object field 110 and in FIG. 3 it is in the region of the right-hand edge thereof.

Consequently the projection objective also receives the light or observation bundle of rays with a principal ray angle (or chief ray angle) which is of the same value in relation to the surface normal of the mask 101. As now the optical system in the scanner and in particular in the projection optical system is of a rotationally symmetrical configuration, that angle, for reasons of symmetry, must always be in that plane formed by the object point which is just being observed of the mask 101 (or the object plane of the projection optical system), with the optical axis.

The bundle of rays reflected at the object point which is respectively being observed is also incident in the projection objective at a (principal ray) angle (in the present example, 6°), but that angle is now so oriented that it is in that plane that is formed with the optical axis of the projection objective. If now as shown in FIGS. 1 through 3 various points are considered along the object field 110, in the shape of a segment of a ring, on the mask 101, then the rays passing into the projection objective do not all extend approximately parallel to each other, but rather are always perpendicular to the object field 110 in the shape of a segment of a ring, as can be seen from FIGS. 1 through 3.

A comparison between the situations in FIGS. 2 and 3 and the situation in FIG. 1 accordingly shows that, for the left-hand and right-hand positions of the object field 110 respectively, the plane that the illumination centroid ray forms with the (principal) ray passing from the mask 101 into the projection objective (that is to say the plane from the bundle of rays incident in the mask 101 and that reflected by the mask 101) is turned in comparison with the situation in FIG. 1 (in which the illuminated position is at the center of the object field 110), wherein it always includes the optical axis of the projection exposure apparatus or the scanner. Thus a movement along the object field 110 in the shape of a segment of a ring requires the above-described plane also to be turned therewith.

In an embodiment the variation in the direction of the centroid ray, that is dependent on the location of incidence of the illumination bundle of rays on the mask, complies with the following condition:

$$\sin(\alpha) = \frac{y}{R},$$

wherein:
x, y denote the co-ordinates of the mask plane,
R denotes the radius of the ring field, and
α denotes the angle between the plane of incidence (formed by the centroid ray which is incident on the mask from the illumination system and the centroid ray reflected by the mask) with the y=0 plane.

In an embodiment the illumination system is designed for operation in the EUV mode.

Although in examples described in the disclosure implementation is effected in a mask inspection apparatus designed for EUV, the disclosure is not restricted thereto. Thus the disclosure can also be applied to a mask inspection apparatus of a higher working wavelength (for example 193 nm) as angle differences in illumination can also occur in relation to such wavelengths so that improved mask inspection can possibly also be achieved by the variation according to the disclosure in the direction of the centroid ray in dependence on the location on the mask.

In some embodiments, systems involving a convergent configuration for the principal rays (that is to say the principal rays pass after reflection at the mask towards the optical axis) can be used. In some embodiments, systems involving divergent principal rays can be used. Systems in which the principal rays pass divergently into the projection objective are known for example from US 2005/0088760 A1 (see FIGS. 91 and 93 of US 2005/0088760 A1).

In some embodiments, the variation in the direction of the centroid ray, that is dependent on the location of incidence of the illumination bundle of rays on the mask, is such that the magnitude of the angle between the centroid ray and the surface normal on the mask is maintained.

In some embodiments, there is provided at least one blade (or aperture stop) which is movable in a predetermined plane of movement to adjust the variation in the direction of the centroid ray, that is dependent on the location of incidence of the illumination bundle of rays on the mask.

In embodiments of the disclosure the blades discussed here and hereinafter can be in the usual way in the form of disks or plates which are provided with holes designed in accordance with the desired illumination setting and which in other respects are non-transmitting. The disclosure however is not restricted thereto. Thus in further embodiments, in place of apertured disks or plates, it is also possible to use partially transmitting and/or partially polarizing components. That is advantageous for example if a variation in the transmission of the scanner as a function of the pupil co-ordinates is to be emulated or in illumination the variation in the illumination strength is to be adjusted over the illumination pupil or also for the emulation of polarizing elements in the (EUV) scanner or the projection exposure apparatus. For continuous adjustment of the numerical aperture the blade itself can also be variable in its shape, for example by virtue of an iris (or iris blade).

In addition, in place of a physical blade, it is also possible to use another suitable device for adjusting the direction of incidence of the illumination rays, for example a per se known multi-mirror array (referred to as an MMA), with a multiplicity of (micro)mirror elements which are adjustable differently from each other.

In an embodiment the above-mentioned predetermined plane of movement is in substantially coplanar relationship with the plane of the mask.

In an embodiment that region of the plane of movement, over which the blade is movable for adjustment of the variation in the direction of the centroid ray, that is dependent on the location of incidence of the illumination bundle of rays on the mask, has a substantially reniform contour.

In an embodiment the blade is designed for adjustment of one or more of the following illumination settings; quadruple illumination setting, dipole illumination setting, annular illumination setting, conventional illumination setting. In that respect in accordance with the usual terminology the term conventional illumination setting is used to denote circular illumination with an intensity which is as uniform as possible within the circle.

In an embodiment the blade is arranged rotatably, which can be advantageous depending on the respective specific configuration of the projection exposure apparatus to be emulated.

In an embodiment the blade is in the form of a variably adjustable blade arrangement, wherein a substructure can be preserved in the brightness distribution of an illumination pupil of an EUV projection exposure apparatus, by adjustment of that blade arrangement.

In an embodiment the blade arrangement has at least two blades movable relative to each other. Those blades can have in particular blade openings of differing shape and/or sizes. Alternatively or additionally one of those blades can have an apodising arm.

In an embodiment the mask is arranged rotatably. In that case a field-dependent displacement of the plane of the illumination system and possibly the projection objective is only still required to adjust different angles of inclination (for example 6°, 9°, etc.).

In a further aspect the disclosure also concerns a projection objective of a mask inspection apparatus, wherein in operation of the mask inspection apparatus the projection objective observes a mask with an observation bundle of rays having a principal ray, wherein that principal ray has a direction dependent on the starting location of the observation bundle of rays on the mask.

In an embodiment there is provided at least one blade movable in a predetermined plane of movement for adjustment of the variation in the direction of the principal ray, that is dependent on the starting location of the observation bundle of rays on the mask.

In an embodiment that region of the plane of movement, over which the blade is movable for adjustment of the variation in the direction of the principal ray, that is dependent on the starting location of the observation bundle of rays on the mask, has a substantially reniform contour.

In an embodiment that plane of movement extends in substantially coplanar relationship with the plane of the mask.

In a further aspect the disclosure also concerns a mask inspection apparatus having an exposure system and a projection objective having the above-described features.

In that respect in an embodiment a blade of the illumination system and a blade of the projection objective are movable in mutually synchronous relationship in opposite directions.

In a further aspect the disclosure also concerns a method of operating a mask inspection apparatus, wherein in operation of the mask inspection apparatus the illumination system illuminates a mask with an illumination bundle of rays having a centroid ray and wherein the projection objective observes said mask with an observation bundle of rays having a principal ray, wherein the direction of the centroid ray and the direction of the principal ray are respectively varied in dependence on the location on the mask.

In a further aspect of the disclosure account is also taken of situations in which the illumination pupil, in its brightness distribution, has substructures deviating from an idealized form (which typically forms the basis in respect of dipole or quadrupole illumination settings). Such a substructure can be governed in particular by using in the illumination system a honeycomb condenser generating a multiplicity of light passages which are superposed in the plane of the mask. Those light passages now do not completely fill the pupil so that it is possible to see individual spots or "illumination peaks".

To take account of that it is also possible in accordance with the disclosure to produce in the plane of the blade not only for example idealized or homogenous dipoles or quadrupoles in the illumination setting, but instead to preserve within the plane of the blade the complete "substructured" illumination distribution.

In accordance with an aspect therefore the disclosure concerns an illumination system of a mask inspection apparatus, wherein the illumination system has at least one blade arrangement which is variably adjustable in such a way that, by adjustment of that blade arrangement, a substructure can be preserved in the brightness distribution of an illumination pupil of an EUV projection exposure apparatus.

In an embodiment the blade arrangement has at least two blades movable relative to each other. Those blades can have in particular blade openings of differing shape and/or sizes. Alternatively or additionally one of those blades can have an apodising arm.

Further configurations of the disclosure are to be found in the description and the appendant claims.

BRIEF DESCRIPTION OF THE DRAWINGS

The disclosure is described in greater detail hereinafter by examples illustrated in the accompanying drawings in which:

FIGS. 7a-7b show further diagrammatic views to explain the disclosure, and FIGS. 8-11 show diagrammatic views to explain embodiments in accordance with a further aspect of the disclosure.

DETAILED DESCRIPTION

Hereinafter reference is made to FIGS. 4 through 7 to describe how, in a mask inspection apparatus in accordance with an example of the disclosure, the above-described illumination conditions which are implemented by the projection exposure apparatus or the scanner (that is to say the variation in the direction of the light incident from the illumination system and the light collected by the projection optical system) are reproduced as well as possible.

Figure 6:
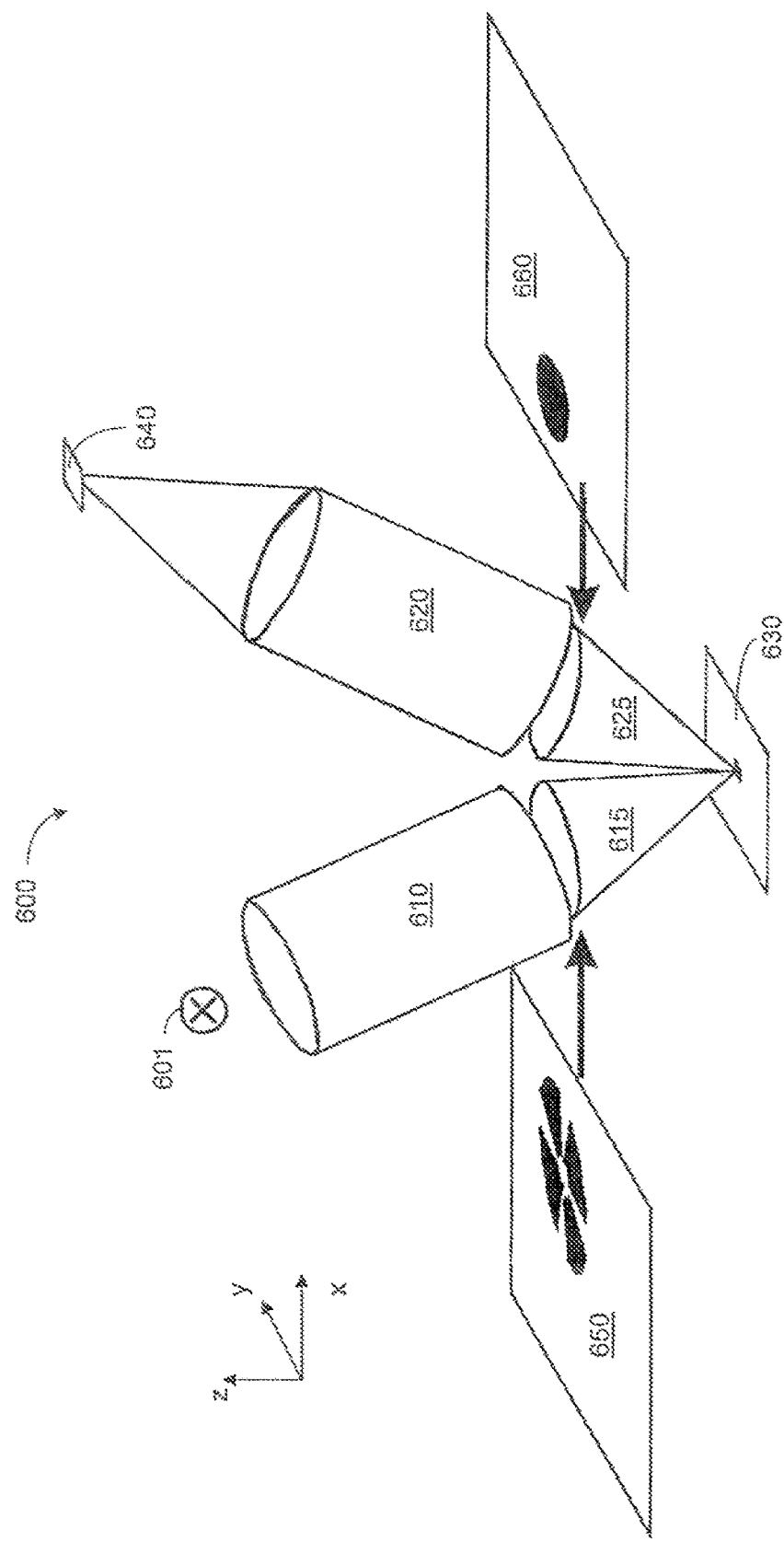
FIG. 6 shows a diagrammatic view of a mask inspection apparatus which is designed for EUV and in which the disclosure is carried into effect.

As is only diagrammatically illustrated in FIG. 6 the mask inspection apparatus 600 includes an illumination system 610 and a projection objective 620, wherein light of an EUV light source 601 passes into the illumination system 610 and an illumination bundle of rays 615 is directed on to a respectively illuminated region or the object field of a mask 630 arranged in the object plane of the projection objective 620, and wherein that object field is imaged (by way of an observation bundle of rays 625) on to a camera (CCD sensor arrangement) 640 by the projection objective 620.

In accordance with the embodiment described by way of example with reference to FIGS. 4 through 7, a respective blade 650 and 660 is used both in the illumination system 610 and also in the projection objective 620 of the mask inspection apparatus 600, as described hereinafter; the respective blade 650 and 660 respectively is movable in a predetermined plane of movement to adjust the variation in the direction of the centroid ray, that is dependent on the location of the incidence of the illumination bundle of rays 615 on the mask 630.

Those blades 650, 660 are in turn preferably respectively placed in a pupil plane and respectively moved in a lateral direction (that is to say in the x-direction and the y-direction in the illustrated co-ordinate system).

As described hereinafter with reference to FIGS. 4 and 5 the respective centroid ray is influenced by means of blades 650, 660 in the illumination system 610 and the projection objective 620 respectively. In that case, the angle of the illumination optical system (that is to say the angle of the centroid ray of the illumination bundle of rays incident on the mask) is adjusted by way of the position of the blade 650 provided in respect of the illumination system 610, and the angle of the centroid ray or main ray of the (observation) bundle of rays in the imaging ray path, which passes into the projection objective, is adjusted by way of the position of the blade 660 provided in respect of the projection objective. The other components of the illumination system 610 and the projection objective 620 (that is to say in particular therefore the EUV light source, mirror, camera and so forth) in contrast do not have to be moved for that purpose. The planes of movement in which the two blades 650, 660 are moved extend parallel to and in coplanar relationship with the mask plane respectively (without the disclosure being restricted thereto).

Figure 1:
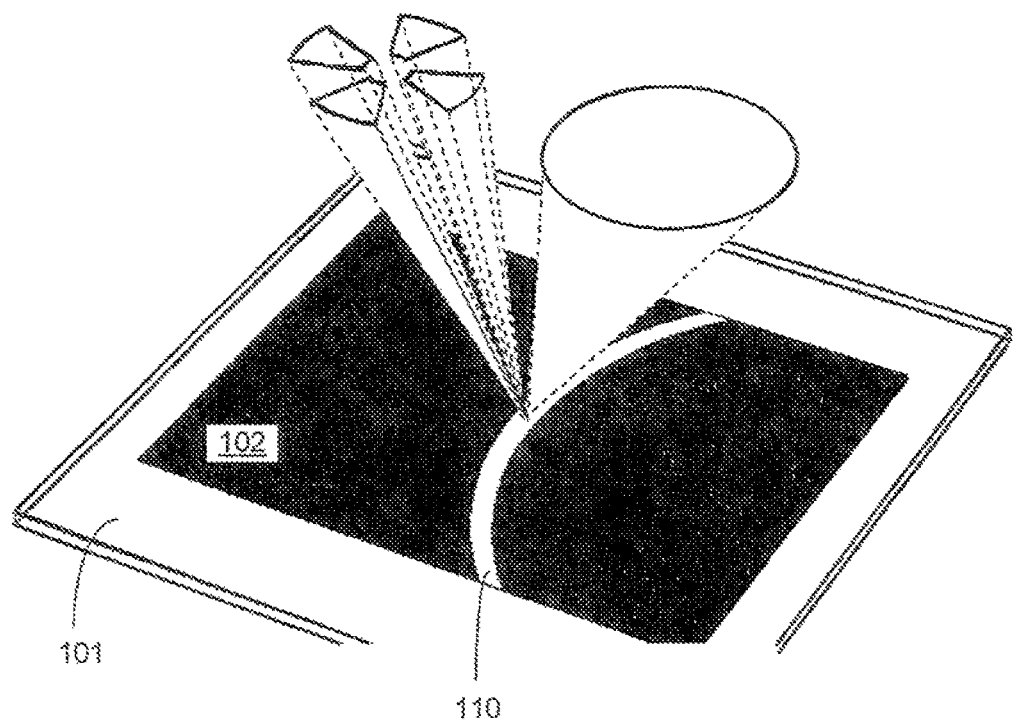
FIGS. 1-5 show diagrammatic views to illustrate and explain the principle of the present disclosure.
Figure 2:
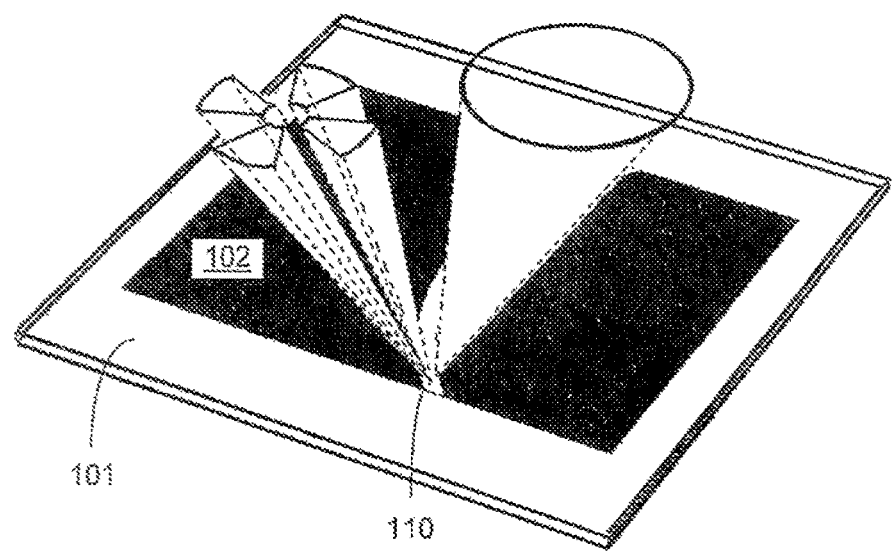
Figure 3:
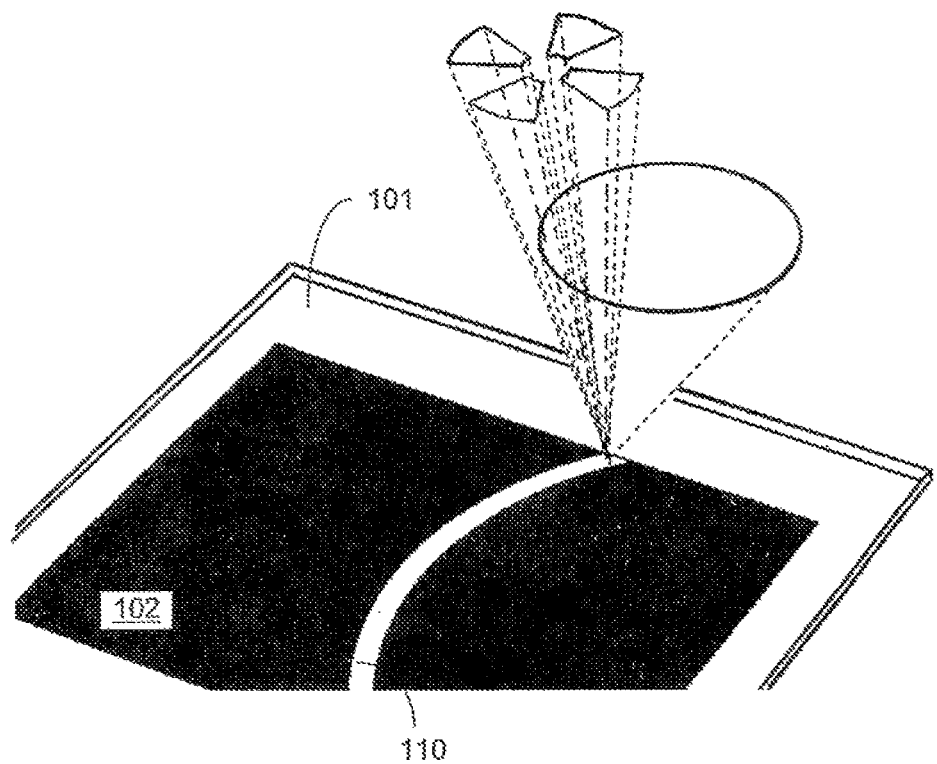
Figure 4:
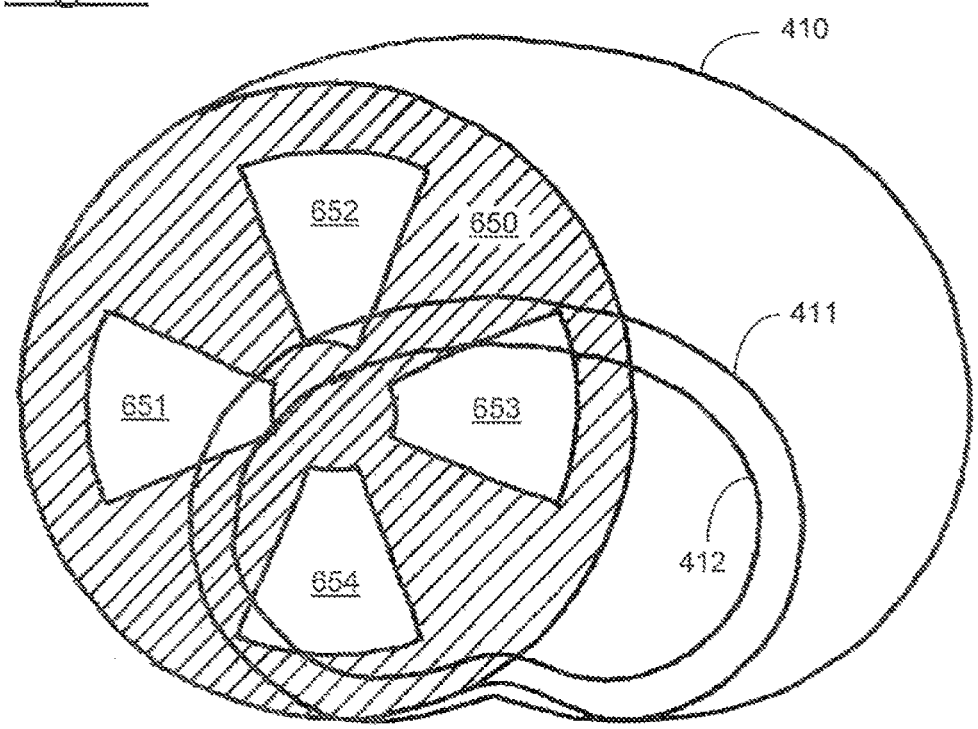

As shown in FIGS. 4 and 6 the blade 650 has openings 651 through 654 corresponding to the desired illumination setting (in the illustrated example a quadrupole illumination setting) and is moved in a plane of movement in accordance with the desired angle which is to be set, that plane of movement in the illustrated example being parallel to the plane of the mask. Reference "410" denotes a region which is used in the course of the entire movement of the blade 650 and which as shown in FIG. 4 can be of a reniform geometry. In that respect for example the illustrated blade 650 can be suitable for a numerical aperture of NA=0.5 whereas the further inwardly disposed or smaller reniform regions 411, 412 which are also shown in FIG. 4 correspond to systems with a smaller pupil or numerical aperture (for example NA=0.32 for the region 411 and NA=0.25 for the region 412). The reniform region 410 (or 411 or 412 respectively) thus also represents the region which prior to use of the blade 650 must be filled with light if or before the blade 650 comes into operation. That signifies that the optical system is generally designed for a larger angular region (that is to say a larger numerical aperture).

Figure 5:
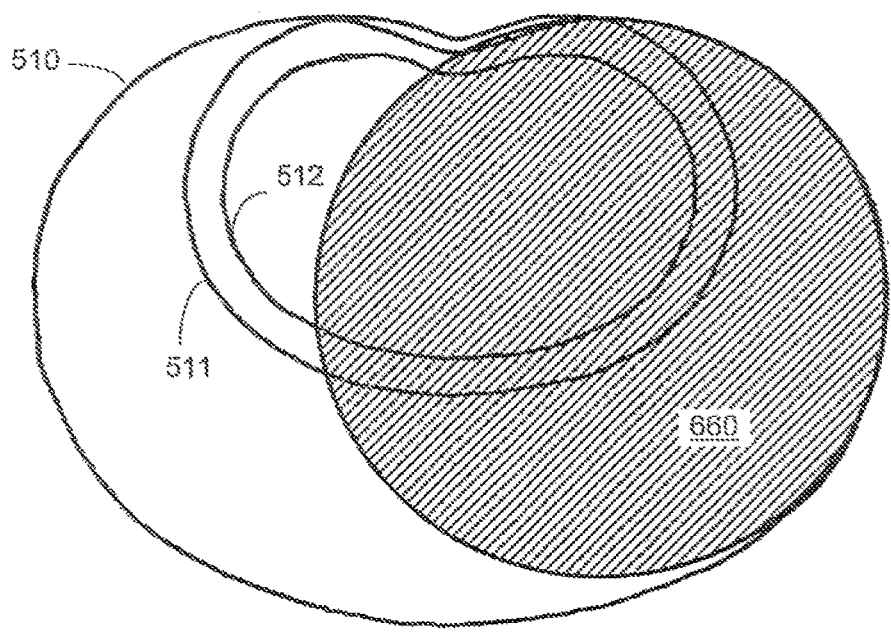

FIG. 5 shows the similar situation for the blade 660 which as shown in FIG. 6 is used in the projection optical system of the mask inspection apparatus but which has a circular geometry and which in turn is similarly moved in the pupil plane of the projection optical system of the mask inspection apparatus (projection objective 620).

Thus in accordance with the disclosure the structures which are to be imaged on the mask and which are written in such a way that they "function" well precisely under the conditions of the projection exposure apparatus are observed under conditions which as far as possible are the same in the mask inspection apparatus, wherein account is taken of the fact that now only a very small field is available and the mask is moved relative to the projection objective not only in the scanner direction but also transversely relative thereto (that is to say from left to right).

In addition the foregoing situation is described as a somewhat different view with reference to FIGS. 7a through 7b.

In that respect in FIG. 7a the optical axis of the projection optical system of the scanner, which extends perpendicularly to the plane of the paper, is identified by $OA_p$. The Figure also shows the scanner slot or the object field 631 which is in the shape of a segment of a ring and which extends concentrically around the optical axis $OA_p$ (so that the optical axis $OA_p$ is at the center point of curvature of the object field 631 in the shape of a segment of a ring).

FIG. 7a also indicates both for the left-hand and the right-hand edge and also for the center of the object field in the shape of a segment of a ring, the respective configuration of the plane of incidence 'A', 'B' and 'C' respectively which each also extend perpendicularly to the plane of the paper and intersect the optical axis $OA_p$. The blades 650 and 660 which are disposed in the pupil plane of the illumination system and the projection objective respectively (that is to say the projection optical system of the mask inspection apparatus) and implement the respective configuration of the plane of incidence 'A', 'B', and 'C' according to the disclosure are indicated here as a plan view.

FIG. 7b shows a corresponding side view in which $OA_M$ denotes the optical axis of the mask inspection apparatus, wherein the object field 631 in the shape of a segment of a ring (to be seen in cross-section here) is disposed at a spacing R from the optical axis of the projection exposure apparatus and is of the width b. The blades in the illumination system or projection objective respectively (that is to say the projection optical system of the mask inspection apparatus) are here denoted by $AS_{ill}$ and $AS_{ob}$ respectively.

The disclosure is thus based on the concept, during the movement of the mask 630 in the course of mask inspection, to simulate the effective direction of incidence of the light, which in the embodiment described here is effected by the blades 650, 660 arranged in the illumination system 610 and the projection objective 620 (projection optical system) of the mask inspection apparatus respectively also being moved. That means, as shown in FIG. 7, that the bundle of rays serving to illuminate the object field 631 in the shape of a segment of a ring on the mask 630 must "stop" in the left-hand portion of the region 410 at the moment at which the observed location on the mask 630 is in the left-hand region of the mask 630 or the object field 631, whereas in corresponding fashion the bundle of rays passing into the optical imaging system (projection optical system of the mask inspection apparatus) must "stop" in the right-hand portion of the region 510.

While now in the course of mask inspection the respective location being inspected moves for example from left to right over the mask 630 a movement of the blades 650 and 660 is effected synchronously and in mutually opposite directions in such a way that gradually the situation shown at the left in FIG. 7a changes over to a mirror-image situation as shown at the right in FIG. 7a, in which the bundle of rays serving to illuminate the mask 630 stops in the right-hand portion of the region 410 and in a corresponding fashion the optical imaging system stops in the left-hand portion of the region 510.

In other words therefore during the scanning procedure the blades 650, 660 are moved over the mask in such a way that depending on the respective mask location which is currently being inspected, different directions of the centroid ray are set in relation to the optical axis. Therefore the blade movement achieves precisely the desired variation in location of the centroid ray, wherein the illumination setting is respectively maintained as a consequence of using the same blade.

It is to be noted in that respect that, with that variation in location of the centroid ray from one location to another on the mask, no variation in magnitude of the angle between the incident centroid ray and the surface normal of the mask is intended, but rather there is a variation in the direction of that angle or centroid ray (in which respect it is to be borne in mind that specifying an angle in terms of magnitude of for example 6° relative to the surface normal of the mask defines a "cone of directions of incidence", and the variation in the direction of the centroid ray takes place along that cone). Accordingly with the variation according to the disclosure preferably the magnitude of the angle between the surface normal on the mask and the centroid ray is retained.

Although hereinbefore reference is made in each case to an arrangement of the blades in the respective pupil plane of the illumination system or the projection objective respectively (that is to say the projection optical system of the mask inspection apparatus) the disclosure is not restricted to an exact arrangement in the pupil plane. Rather, having regard to the very small size of the object field in the microscope, to a good degree of approximation each plane remote from the mask or the object plane can be viewed as the pupil plane. For ease of implementation (and without the disclosure being restricted thereto) it is therefore appropriate for the blades 650, 660 each to be arranged at a relatively large spacing relative to the mask 630 and as diagrammatically shown in FIG. 6 to be disposed outside the remainder of the optical arrangement of the illumination system 610 and the projection objective 620 respectively (that is to say the projection optical system of the mask inspection apparatus), in which respect in particular there does not have to be any additional imaging optical means between the blade 650 and the blade 660 respectively and the illumination system and the projection objective respectively (projection optical system of the mask inspection apparatus). The disclosure however is not restricted thereto so that in other embodiments a further (imaging) optical system can also be provided between blade and illumination system or projection optical system of the mask inspection apparatus.

As regards the respective planes in which the blades 650 and 660 are moved, this can involve the same plane or also mutually coplanar planes. In addition those planes can be coplanar in relation to the object plane and the mask plane respectively. The disclosure however is also not restricted thereto, that is to say under some circumstances it may also be appropriate for those planes to be tilted in comparison with the reticle and/or in relation to each other.

A mathematical description of the variation in the centroid ray in dependence on the location on the mask can be as follows: if x and y are used to denote the co-ordinates of the mask plane and z is used to denote the co-ordinate perpendicular to the mask plane, and if in that respect x is used to denote the co-ordinate along which scanning is effected, the active surface of the mask extends in the y-direction from −b/2 through +b/2, wherein b denotes the scanner slot width (which can be of a value by way of example of 104 mm).

The direction of the centroid ray of the illumination bundle of rays can be defined by way of the vector $(c_x, c_y, c_z)$, wherein $c_x^2 + c_y^2 + c_z^2 = 1$ and $c_x$ denotes the projection on to the x-axis, and so forth (=so-called "directional cosine representation" with standardized directional vector c).

With a ring field radius R (defined as the spacing of the center of the ring field from the optical axis of the projection objective) the resulting formulae are as follows:

$$\frac{c_x}{\sqrt{1-c_z^2}} = \sqrt{\left(1-\left(\frac{y}{R}\right)^2\right)} \quad (1)$$

and $$\frac{c_y}{\sqrt{1-c_z^2}} = \frac{y}{R} \quad (2)$$

wherein $c_z$ corresponds to the cosine of the angle of incidence which can involve typical values of at the present time between 6° and about 8°-9° or thereabove (for higher numerical apertures).

An example of calculation for the edge of the mask can be as follows: maximum value for y: $y_{Max}=52$ mm, R (=ring field radius)=100 mm and $c_x=0.089$, $c_y=0.054$ and $c_z=\cos(6°)=0.995$.

The angle α which the plane of incidence (formed by the ray which is incident on the mask from the illumination system and which is emergent, that is to say entering in the projection objective) includes with the y=0 plane is given by:

$$\tan(\alpha) = \frac{c_y}{c_x} \quad (3)$$

or also by $$\sin(\alpha) = \frac{y}{R} \quad (4)$$

wherein in the foregoing example α=31.2 degrees.

In accordance with a further aspect of the disclosure account is also taken of situations in which the illumination pupil in its brightness distribution has substructures deviating from an idealized form. Such a substructure can be governed in particular by using in the illumination arrangement a honeycomb condenser producing a multiplicity of light passages which are superposed in the plane of the mask. Those light passages now do not completely fill the pupil so that it is possible to see individual spots or "illumination peaks".

FIG. 8 shows in that respect an example of a typical EUV pupil at two different field points. The numbers respectively shown in the white circles represent the different levels of brightness of the pupil parcels and their field dependency.

To take account of the above-described situation it is also possible in accordance with the disclosure to produce not only idealized illumination distributions (for example with homogeneous dipole or quadrupole settings) in the aperture plane of the mask inspection apparatus, but also to preserve the complete "substructured" illumination distribution within the aperture plane.

Figure 9:
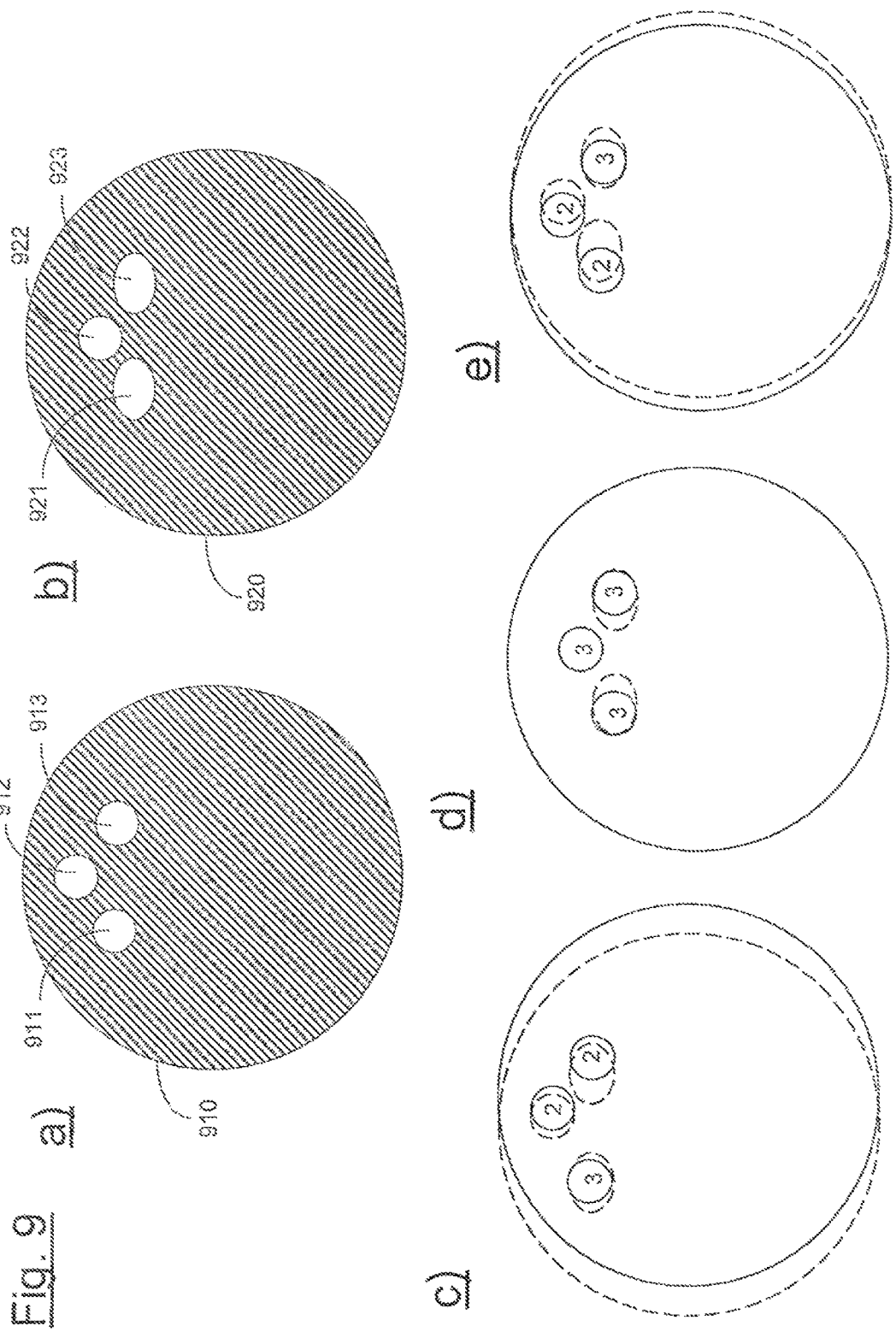
Figure 10:
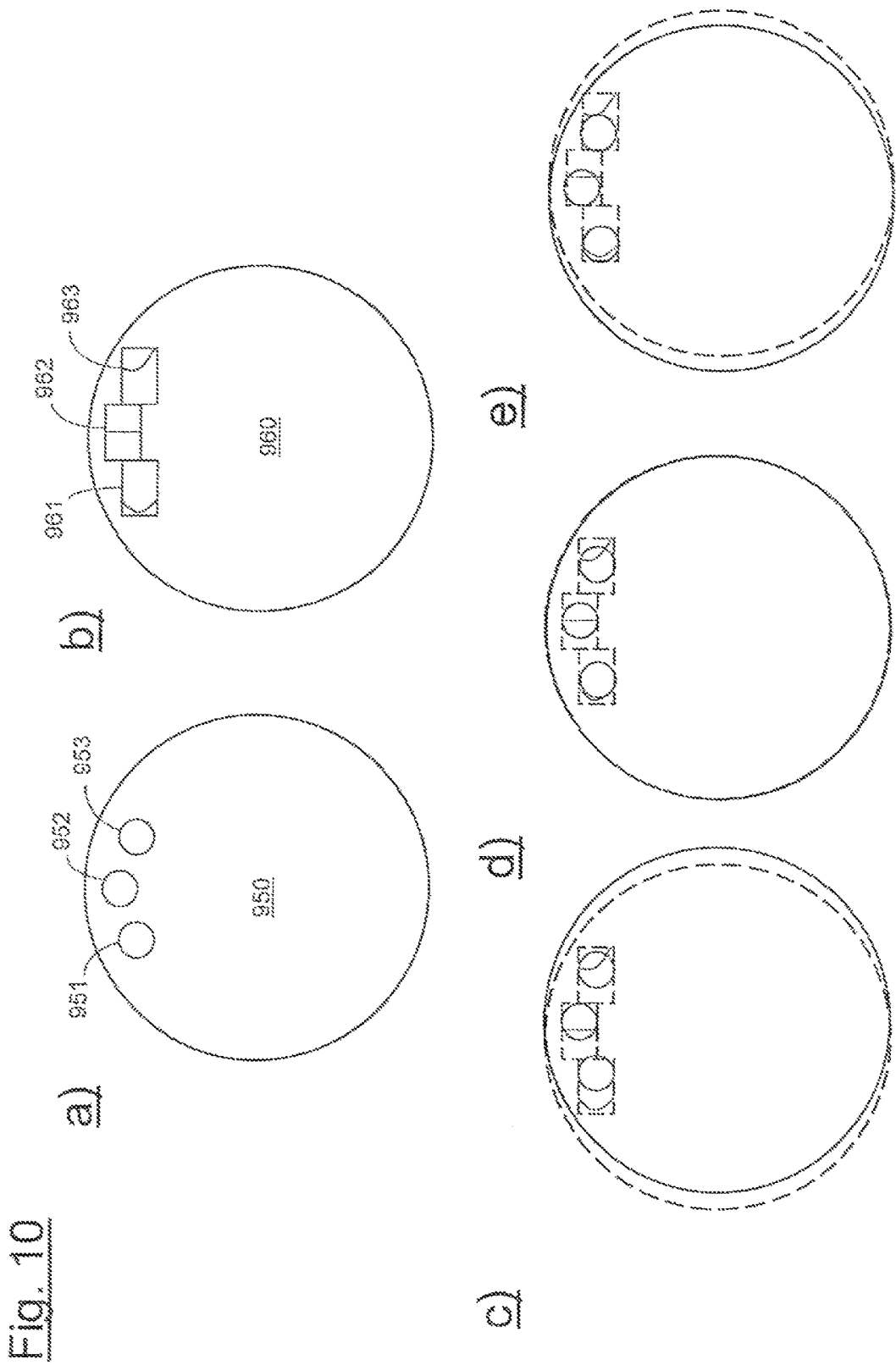
Figure 11:
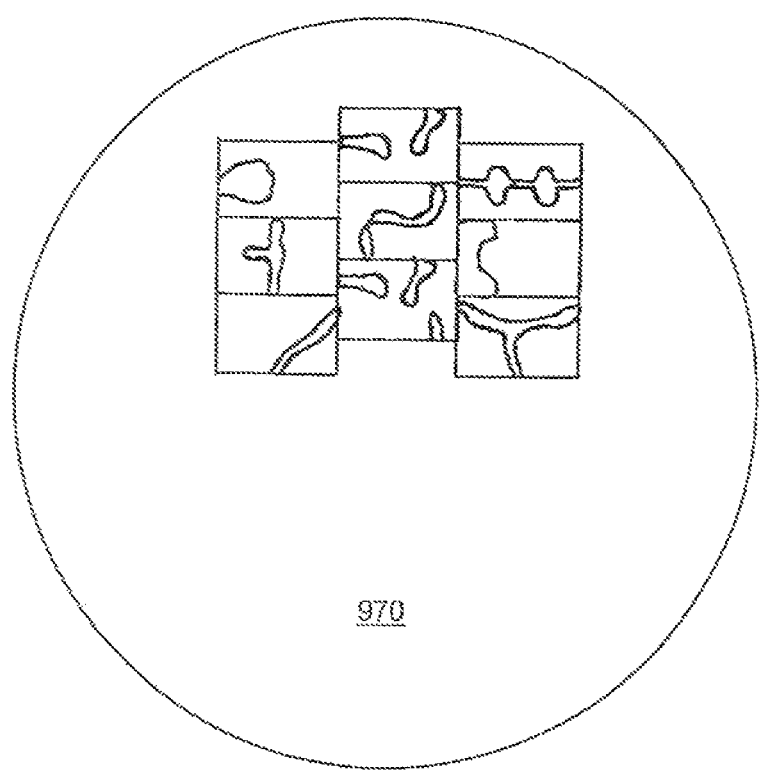

Reference will now be made hereinafter to FIGS. 9 through 11 to describe embodiments which serve to reproduce the above-described parcellings of the pupil illumination including the fluctuations in intensity in mask inspection.

For that purpose in some embodiments, instead of a conventional one-part blade, a blade arrangement comprising at least two blades (in further embodiments therefore also three, four or more blades) is used, wherein those blades are so-to-speak "connected in series" and are of such a design configuration that relative displacement and/or rotation of the blades makes it possible to adjust the effective opening of the pupil parcels and thus the integral brightness or light efficiency thereof.

Referring to FIGS. 9a and 9b, the blade arrangement is made up of two blades 910, 920 which are arranged in succession in the light propagation direction and which each have three holes 911-913 and 921-923 respectively (for example a respective hole for each pupil parcel), wherein however both blades 910, 920 have holes of differing shape. Thus the first blade 910 which is shown only diagrammatically and by way of example has three circular holes 911-913, whereas the second blade 920 has a circular hole 922 between two elongate holes 921 and 923. The individual blades of the blade arrangement do not necessarily have to be arranged in directly successive relationship.

As shown in FIGS. 9c, 9d and 9e a variation in the effective hole size for each pupil parcel and thus adjustment of the integral brightness or light efficiency can be achieved by relative displacement of the blades 910, 920 in a horizontal direction. If for example the size of the holes 911-913 in the first blade 910 is quantified with a (notional) value 3, then for example the hole size can be viewed as a function of the horizontal displacement as specified in Table 1:

TABLE 1

|  | Displacement towards the left | No displacement | Displacement towards the right |
| --- | --- | --- | --- |
| Top left | 3 | 3 | 2 |
| Top center | 2 | 3 | 2 |
| Top right | 2 | 3 | 3 |

Thus in accordance with the disclosure a substructuring as described hereinbefore of the pupil illumination in the mask inspection apparatus can be afforded.

In a further embodiment diagrammatically illustrated in FIG. 10 it is also possible to provide a variable hole size and thus a variation in the effective opening of the pupil parcels and thus the integral brightness or light efficiency, by at least one blade of at least two blades 950, 960 having at least one apodising arm (here the second blade 960 shown in FIG. 10b) which partially covers the hole opening and thus leads to an effective reduction in the size of the hole. Thus the effective hole size is altered passage-wise by relative displacement of the second blade 960 relative to the first blade 950 in FIG. 10a, by the hole size in the first blade 950 being reduced by the area of the arm covering it.

FIG. 11 is a merely diagrammatic view showing further possible configurations of an arm on a blade 970.

In a further embodiment a blade arrangement for variable adjustment of the intensity in the above-described subpupils or substructures can also be implemented in a (single-stage) blade having a multiplicity of variably adjustable iris blades which are adjustable individually or in their entirety by suitable actuators.

It will be appreciated that the above-described concept of providing the complete "substructured" illumination distribution within the mask inspection apparatus can also be implemented independently of the concept according to the disclosure of varying the direction of the centroid ray in dependence on the location on the mask. In accordance with a further aspect therefore the disclosure also concerns a mask inspection apparatus in which a substructure of the illumination distribution is afforded, preferably by using a suitable blade arrangement, without at the same time the variation in the direction of the centroid ray in dependence on the location on the mask also being implemented.

Even if the invention has been described by means of specific embodiments numerous variations and alternative embodiments will be apparent to the man skilled in the art, for example by the combination and/or exchange of features of individual embodiments. Accordingly the man skilled in the art will appreciate that such variations and alternative embodiments are also embraced by the present invention and the scope of the invention is limited only in the sense of the accompanying claims and equivalents thereof.

The invention claimed is:

1. An illumination system of a mask inspection apparatus, wherein the illumination system is configured to, in operation of the mask inspection apparatus, illuminate a mask with an illumination bundle of rays which has a centroid ray; and wherein the illumination system is further configured such that, during the operation of the mask inspection apparatus, said centroid ray has a direction dependent on the location of the incidence of the illumination bundle of rays on the mask, in which the centroid ray has at least two different directions for different locations of the incidence of the illumination bundle of rays on the mask, and there is a predetermined relationship between the direction of the centroid ray and the location of incidence of the illumination bundle of rays on the mask, such that the centroid ray has a first direction for a first location of incidence of the illumination bundle of rays on the mask, and the centroid ray has a second direction different from the first direction for a second location different from the first location of incidence of the illumination bundle of rays on the mask.

2. The illumination system of claim 1 in which the maximum angle between the planes of incidence of two bundles of rays incident on different locations of the mask is at least 3°.

3. The illumination system of claim 1 in which the maximum angle between the centroid rays of two bundles of rays incident on different locations of the mask is at least 3°.

4. The illumination system of claim 1 in which the mask that is analyzed in the operation of the mask inspection apparatus is designed for use with an illumination region in the form of a segment of a ring in a projection exposure apparatus.

5. The illumination system as of claim 4 in which the variation in the direction of the centroid ray, that is dependent on the location of incidence of the illumination bundle of rays on the mask, complies with the condition:

$$\sin(\alpha) = \frac{y}{R}$$

wherein:
y denotes the co-ordinate of the mask plane,
R denotes the radius of the ring field, and
α denotes the angle between the plane of incidence, formed by the centroid ray which is incident on the mask from the illumination system and that which is reflected by the mask, with the y =0 plane.

6. The illumination system of claim 1 in which the illumination system is designed for operation in an extreme ultra-violet (EUV) mode.

7. The illumination system of claim 1 in which the variation in the direction of the centroid ray, that is dependent on the location of incidence of the illumination bundle of rays on the mask, is such that the magnitude of the angle between the centroid ray and the surface normal on the mask is maintained.

8. The illumination system of claim 1 in which there is provided at least one blade movable in a predetermined plane of movement for adjustment of the variation in the direction of the centroid ray, that is dependent on the location of incidence of the illumination bundle of rays on the mask.

9. The illumination system of claim 1 in which the illumination system comprises at least one blade movable for adjustment of the variation in the direction of the centroid ray during the operation of the mask inspection apparatus, wherein the illumination system is configured such that when the at least one blade is at a first location, the incidence of the illumination bundle of rays is at the first location on the mask and the centroid ray has the first direction, and when the same at least one blade is at a second location, the incidence of the illumination bundle of rays is at the second location on the mask and the centroid ray has the second direction.

10. The illumination system of claim 1 in which a magnitude of an angle between the incident centroid ray and a surface normal of the mask remains constant when the direction of the centroid ray changes from the first direction to the second direction.

11. The illumination system of claim 10 in which the constant magnitude of the angle between the incident centroid ray and the surface normal of the mask defines a cone of directions of incidence, and a variation of the direction of the centroid ray takes place along the cone of directions of incidence.

12. The illumination system of claim 1 in which for at least a portion of the mask, the direction of the centroid ray varies continuously as the location of incidence of the illumination bundle of rays on the mask varies continuously.

13. The illumination system of claim 1, wherein an object field is in a shape of a segment of a ring that extends concentrically around an optical axis, and wherein when the incidence of the illumination bundle of rays is at the first location on the mask, the incident centroid ray propagates along a first plane of incidence, when the incidence of the illumination bundle of rays is at the second location on the mask, the incident centroid ray propagates along a second plane of incidence, and the first plane of incidence intersects the second plane of incidence at the optical axis.

14. The illumination system of claim 1 in which the direction of the centroid ray is a function of the location of the incidence of the illumination bundle of rays on the mask.

15. An illumination system of a mask inspection apparatus,
wherein the illumination system is configured to, in operation of the mask inspection apparatus, illuminate a mask with an illumination bundle of rays which has a centroid ray;
wherein the illumination system is further configured such that, during the operation of the mask inspection apparatus, said centroid ray has a direction dependent on the location of the incidence of the illumination bundle of rays on the mask, in which the centroid ray has at least two different directions for different locations of the incidence of the illumination bundle of rays on the mask, and there is a predetermined relationship between the direction of the centroid ray and the location of incidence of the illumination bundle of rays on the mask, such that the centroid ray has a first direction for a first location of incidence of the illumination bundle of rays on the mask, and the centroid ray has a second direction different from the first direction for a second location different from the first location of incidence of the illumination bundle of rays on the mask;
wherein the illumination system comprises at least one blade movable in a predetermined plane of movement for adjustment of the variation in the direction of the centroid ray during the operation of the mask inspection apparatus, dependent on the location of incidence of the illumination bundle of rays on the mask.

16. The illumination system of claim 15 in which said plane of movement extends in substantially coplanar relationship with the mask plane.

17. The illumination system of claim 15 in which a region of the plane of movement, over which the blade is movable for adjustment in the variation in the direction of the centroid ray, that is dependent on the location of incidence of the illumination bundle of rays on the mask, has a substantially reniform contour.

18. The illumination system of claim 15 in which the blade is adapted for adjustment of at least one of quadrupole illumination setting, dipole illumination setting, annular illumination setting, or conventional illumination setting.

19. The illumination system of claim 15 in which the blade is arranged rotatably.

20. The illumination system of claim 15 in which the blade is in the form of a variably adjustable blade arrangement, wherein by adjustment of said blade arrangement a substructure can be afforded in the brightness distribution of an illumination pupil of an extreme ultra-violet (EUV) projection exposure apparatus in the mask inspection apparatus.

21. The illumination system of claim 20 in which said blade arrangement has at least two blades movable relative to each other.

22. The illumination system of claim 21 in which said blades have at least one of blade openings of differing shape or blade openings of differing sizes.

23. The illumination system of claim 21 in which at least one of said blades has an apodising arm.

24. The illumination system of claim 15 in which the mask is arranged rotatably.

25. The illumination system of claim 15 in which the illumination system is configured such that when the at least one blade is at a first location, the incidence of the illumination bundle of rays is at the first location on the mask and the centroid ray has the first direction, and when the same at least one blade is at a second location, the incidence of the illumination bundle of rays is at the second location on the mask and the centroid ray has the second direction.

26. The illumination system of claim 15 in which a magnitude of an angle between the incident centroid ray and a surface normal of the mask remains constant when the direction of the centroid ray changes from the first direction to the second direction.

27. The illumination system of claim 26 in which the constant magnitude of the angle between the incident centroid ray and the surface normal of the mask defines a cone of directions of incidence, and a variation of the direction of the centroid ray takes place along the cone of directions of incidence.

28. The illumination system of claim 15 in which for at least a portion of the mask, the direction of the centroid ray varies continuously as the location of incidence of the illumination bundle of rays on the mask varies continuously.

29. The illumination system of claim 15, wherein an object field is in a shape of a segment of a ring that extends concentrically around an optical axis, and wherein when the incidence of the illumination bundle of rays is at the first location on the mask, the incident centroid ray propagates along a first plane of incidence, when the incidence of the illumination bundle of rays is at the second location on the mask, the incident centroid ray propagates along a second plane of incidence, and the first plane of incidence intersects the second plane of incidence at the optical axis.

30. The illumination system of claim 15 in which the direction of the centroid ray is a function of the location of the incidence of the illumination bundle of rays on the mask.

31. A projection objective of a mask inspection apparatus, wherein the projection objective is configured to, in operation of the mask inspection apparatus, observe a mask with an observation bundle of rays having a principal ray, and
wherein the projection objective is further configured such that, in the operation of the mask inspection apparatus, said principal ray has a direction dependent on the starting location of the observation bundle of rays on the mask, in which the principal ray has at least two different directions for different starting locations of the observation bundle of rays on the mask, and there is a predetermined relationship between the direction of the principal ray and the starting location of the observation bundle of rays on the mask, such that the principal ray has a first direction for a first starting location of the observation bundle of rays on the mask, and the principal ray has a second direction different from the first direction for a second starting location different from the first starting location of the observation bundle of rays on the mask.

32. The projection objective of claim 31 in which the projection objective is designed for operation in an extreme ultra-violet (EUV) mode.

33. The projection objective of claim 31 in which there is provided at least one blade which is movable in a predetermined plane of movement for adjustment of the variation in the direction of the principal ray, that is dependent on the starting location of the observation bundle of rays on the mask.

34. The projection objective of claim 33 in which the region of the plane of movement, over which the blade is movable for adjustment of the variation in the direction of the principal ray, that is dependent on the starting location of the observation bundle of rays on the mask, has a substantially reniform contour.

35. The projection objective of claim 33 in which said plane of movement extends in substantially coplanar relationship with the mask plane.

36. The projection objective of claim 31 in which the projection objective comprises at least one blade movable for adjustment of the variation in the direction of the principal ray, wherein the projection objective is configured such that when the at least one blade is at a first location, the starting location of the observation bundle of rays is at the first location on the mask and the principal ray has the first direction, and when the same at least one blade is at a second location, the starting location of the observation bundle of rays is at the second location on the mask and the principal ray has the second direction.

37. The illumination system of claim 31 in which for at least a portion of the mask, the direction of the principal ray varies continuously as the starting location of the observation bundle of rays on the mask varies continuously.

38. A mask inspection apparatus comprising:
an illumination system configured to, in operation of the mask inspection apparatus, illuminate a mask with an illumination bundle of rays which has a centroid ray, wherein the illumination system is further configured such that, during the operation of the mask inspection apparatus, said centroid ray has a direction dependent on the location of the incidence of the illumination bundle of rays on the mask, in which the centroid ray has at least two different directions for different locations of the incidence of the illumination bundle of rays on the mask; and
a projection objective configured to, in the operation of the mask inspection apparatus, observe the mask with an observation bundle of rays having a principal ray, wherein the projection objective is further configured such that, in the operation of the mask inspection apparatus, said principal ray has a direction dependent on the starting location of the observation bundle of rays on the mask, in which the principal ray has at least two different directions for different starting locations of the observation bundle of rays on the mask, in which a first blade of the illumination system is configured to be movable in a first plane and a second blade of the projection objective is configured to be movable in a second plane, and the first blade and the second blade are configured to move synchronously relative to each other in opposite directions in the respective planes.

39. The mask inspection apparatus of claim 38 in which the illumination system and the projection objective are configured such that when the first blade is at a first location, the observation bundle of rays has a first starting location on the mask, the principal ray has a first direction, and the second blade is at a second location, and when the first blade is at a third location different from the first location, the observation bundle of rays has a second starting location on the mask, the principal ray has a second direction, and the second blade is at a fourth location different from the second location.

40. A method of operating a mask inspection apparatus, comprising:
illuminating, using an illumination system, a mask with an illumination bundle of rays having a centroid ray, and
observing, using a projection objective, said mask with an observation bundle of rays having a principal ray,
wherein, during a movement of the mask in the course of mask inspection, the direction of the centroid ray and the direction of the principal ray are respectively varied in dependence on the location on the mask being illuminated and observed, there is a predetermined relationship between the direction of the centroid ray and the location on the mask being illuminated, and there is a predetermined relationship between the direction of the principal ray and the location on the mask being illuminated, such that when a first location on the mask is illuminated, the centroid ray has a first direction and the principal ray has a second direction, and when a second location different from the first location on the mask is illuminated, the centroid ray has a third direction different from the first direction and the principal ray has a fourth direction different from the second direction.

41. The method of claim 40, comprising:
moving a first blade of the illumination system to a first location and a second blade of the projection objective to a second location to cause the first location on the mask to be illuminated, and causing the centroid ray to have the first direction and the principal ray to have the second direction; and
moving the first blade to a third location different from the first location and the second blade to a fourth location different from the second location to cause the second location on the mask to be illuminated, and causing the centroid ray to have the third direction and the principal ray to have the fourth direction.

42. The method of claim 41 in which moving the first blade comprises moving the first blade in a first predetermined plane of movement, and moving the second blade comprises moving the second blade in a second predetermined plane of movement.

43. The method of claim 42 in which the first predetermined plane and the second predetermined plane are at least one of (i) the same plane, or (ii) parallel to each other.

44. An illumination system of a mask inspection apparatus wherein the illumination system comprises at least one blade arrangement which is variably adjustable in such a way that a substructure can be afforded in the brightness distribution of an illumination pupil of an extreme ultraviolet (EUV) projection exposure apparatus by adjustment of said blade arrangement;

wherein the illumination system is configured such that, during operation of the mask inspection apparatus, the blade arrangement is varied in dependence on the location of the incidence of an illumination bundle of rays on a mask being illuminated by the illumination system, and there is a predetermined relationship between the blade arrangement and the location of incidence of the illumination bundle of rays on the mask; and wherein the blade arrangement comprises at least one of (i) two or more blades that are arranged in succession in the light propagation direction, in which each blade has two or more holes, and the relative position of the two or more blades is varied in dependence on the location of the incidence of the illumination bundle of rays on the mask, or (ii) a single-stage blade having multiple adjustable iris blades, in which the iris blades are varied in dependence on the location of the incidence of the illumination bundle of rays on the mask.

45. The illumination system of claim 44 in which the substructure of the brightness distribution of the illumination pupil comprises illumination peaks.

* * * * *

UNITED STATES PATENT AND TRADEMARK OFFICE
CERTIFICATE OF CORRECTION

PATENT NO. : 10,114,293 B2  
APPLICATION NO. : 13/587077  
DATED : October 30, 2018  
INVENTOR(S) : Heiko Feldmann et al.

Page 1 of 1

It is certified that error appears in the above-identified patent and that said Letters Patent is hereby corrected as shown below:

On the Title Page

Column 1, (75) Inventors, Line 6, delete "Alttusried (DE)" and insert -- Altusried (DE) --

In the Claims

<u>Column 15</u>  
Line 55, in Claim 37, delete "illumination system" and insert -- projection objective --

Signed and Sealed this  
Eighth Day of January, 2019

Andrei Iancu  
*Director of the United States Patent and Trademark Office*